United States Patent [19]

Antony et al.

[11] Patent Number: 4,539,754
[45] Date of Patent: Sep. 10, 1985

[54] AUXOLOGICAL MEASURING APPARATUS

[75] Inventors: Gabriel Antony, Coogee; Richard B. Frost, Eastwood, both of Australia

[73] Assignee: Unisearch Limited, Eastwood,

[21] Appl. No.: 542,893

[22] Filed: Oct. 17, 1983

[30] Foreign Application Priority Data

Oct. 15, 1982 [AU] Australia .................. PF6369

[51] Int. Cl.³ ............................................. G01B 7/02
[52] U.S. Cl. .................. 33/169 R; 33/143 L; 33/515
[58] Field of Search ............ 33/169 R, 174 D, 143 R, 33/143 M, 143 L; 128/781, 782

[56] References Cited

U.S. PATENT DOCUMENTS 3,196,551 7/1965 Provost et al. .................... 33/174 D
3,500,547 3/1970 Haagen ............................ 33/143 L

FOREIGN PATENT DOCUMENTS 941542 7/1948 France ........................... 33/174 D
0602052 7/1978 Switzerland ..................... 33/169 R Primary Examiner—Harry N. Haroian

[57] ABSTRACT

An auxological measuring apparatus in which there is provided a flat surface which is preferably horizontal, having on it a plate arranged for contact by the feet of a person with his back against the surface and on the case of a horizontal surface lying supine on it, there being a carriage linearly moveable on the surface which can be brought into contact with the person's head. An electronic transducer is associated with the carriage and is arranged to produce an electric signal indicative of the distance between the carriage and the surface and it is associated with electronic circuitry arranged to process the signal and to provide a visible indication of the distance and thus of the height of the person on the surface. A side table may be provided for attachment to the surface so that a person may lie on the surface and the side table with arms outstretched on the table so that an arm span mesurement can be made.

6 Claims, 7 Drawing Figures

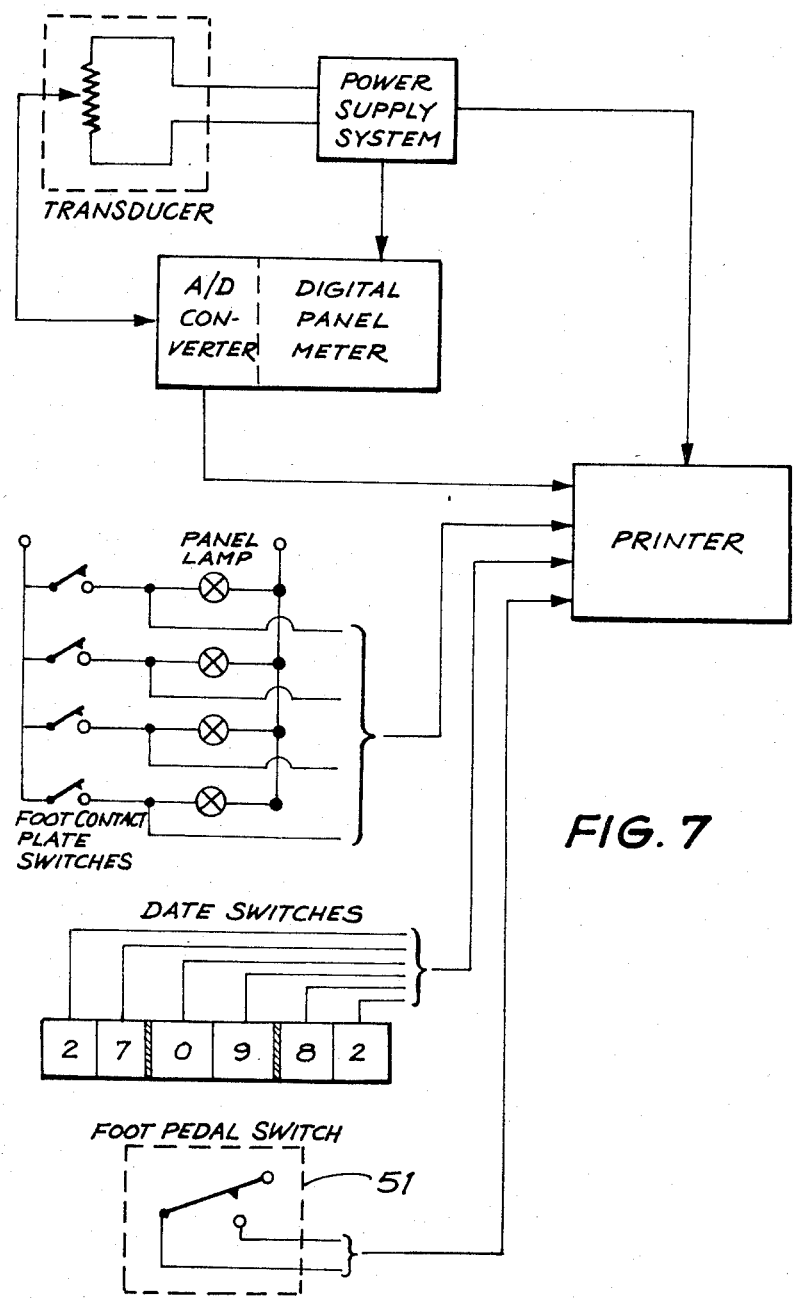

AUXOLOGICAL MEASURING APPARATUS

The present invention relates to auxological measurement apparatus, that is to say to an apparatus for measuring somatic growth in humans and more particularly children and adolescents.

Somatic growth in the individual child has long been recognised as an excellent indicator of general health as well as a useful monitor of various specific disorders. However, for growth rate to achieve its full clinical potential, measurements need to be reliable, in terms of accuracy and repeatability, so that small differences between measurements taken at successive meetings with a particular subject will give reliable values for growth rate. It is recognised that a live human being, possessing resilience and many degrees of freedom of joint mobility, is one of the most difficult objects to measure accurately; this requires the availability of suitable measuring equipment, and its correct operation in conformity with a suitable standard technique. Neither of these conditions has been widely satisfied hitherto in clinical settings, wherein devices have often been conceptually crude, with low rigidity and control levels, and either low resolution or a high probability of mis-reading, and they have often been used by people without adequate specific training. As the resulting measurements have been tangibly unreliable, their clinical potential has not been achieved.

The object of the invention is to provide an improved auxological measuring apparatus for measuring major body dimensions. The invention is considered to present advantages when applied to the measurement of parameters such as supine length, leg length and arm span, such measurements being made with the subject supported on a horizontal surface. The invention is, however, applicable in some aspects to traditional forms of apparatus intended mainly for use in the measurement of stature, i.e. standing height.

The present invention consists in auxological measuring apparatus comprising means including a flat surface against which the soles and heels of the feet of a human subject to be measured are placed, means movable linearly to and from said surface, said last mentioned means being adapted for contacting the subject's head, electronic transducer means associated with said movable means arranged to produce an electric signal indicative of the distance between said movable means and said surface, electronic circuitry arranged to process said signal and to provide a visible indication of said distance. Preferably printing means are provided to furnish a printed record of said indication.

It is preferred that the apparatus is constructed to measure parameters of the subject's body when in a supine position.

In order to enable the invention to be better understood a preferred form thereof is hereinafter described by way of example with reference to the accompanying drawings in which:

FIG. 7 is a schematic view of the electrical system associated with the apparatus.

Figure 1:
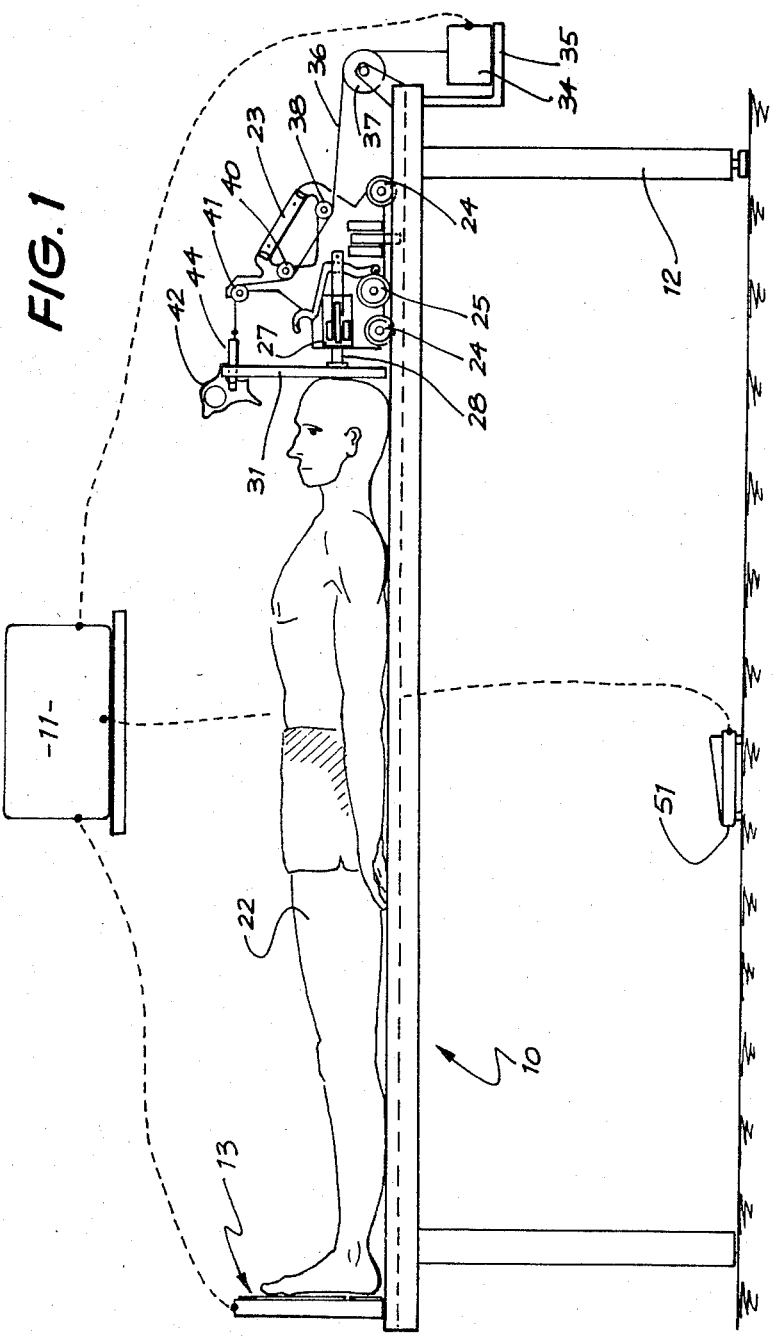
FIG. 1 is a view in elevation of apparatus according to the invention with a subject in position for the making of a supine length measurement.
Figure 4:
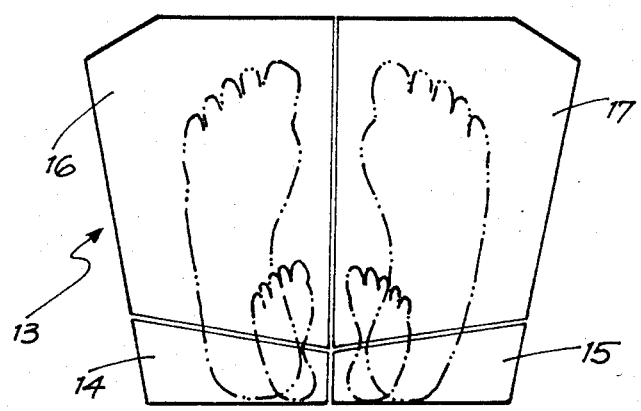
FIG. 4 is a view in elevation of the foot contact box forming part of the apparatus.

In a preferred form the apparatus consists of a horizontal table 10, which is free-standing and preferably in an air-conditioned temperature-controlled room, and a table-or-shelf-mounting console 11, see FIG. 1. The table 10 is built onto a robust rigid steel frame with one adjustable leg 12 to accommodate a slightly uneven floor, and has a smooth polished wooden top surface. This is well supported on the steel frame by frequent shimmed bearers (not shown). At the foot end of the table 10, corresponding to the operator's left hand, is a foot contact box 13. This provides a flat surface onto which the feet can press and by which they will be guided to an orientation which is perpendicular to the table surface. The contact surface consists of four stainless steel plates 14, 15, 16 and 17 which are hinged and lightly spring loaded so that they deflect slightly into a truly planar configuration under the influence of the foot contact, thereby actuating micro-switches behind the plates to demonstrate via a lamp array and a printer (not shown) in the console 11 that the feet are in the proper position. The shapes, hinge axes and switch positions have been designed so that all four plates are equally operable by the right and left heels and MTP joints of a small young child and a large near-adult, see FIG. 4. The foot contact box is of rigid construction to minimise its deflection under the foot contact load. Provision is made in the rear of the box for the insertion of two jack-screws to brace the top end of the contact box against an adjacent wall if one is available, although this is not seen as being essential.

The top of the table 10 contains marked lines 18 (see FIG. 3) running axially for its full length, these are spaced equidistant from the table centreline and provide a guide to the operator when positioning a subject on the table. Along the table centreline is a gap 21 between two timber sections forming the table surface. Centrally and vertically located in this gap is one flange of an extruded aluminium angle which runs axially along the table. This is bolted to the steel frame at a number of locations and is shimmed so that it is straight and its top surface is flush with the wooden table top. A satin cloth (not shown) with a low co-efficient of friction against itself is thrown over the table top and arranged with a large amount of gather. The subject 22 lies on this, and has limited but adequate freedom of movement in any direction at each contact point, at a low level of friction.

Figure 5:
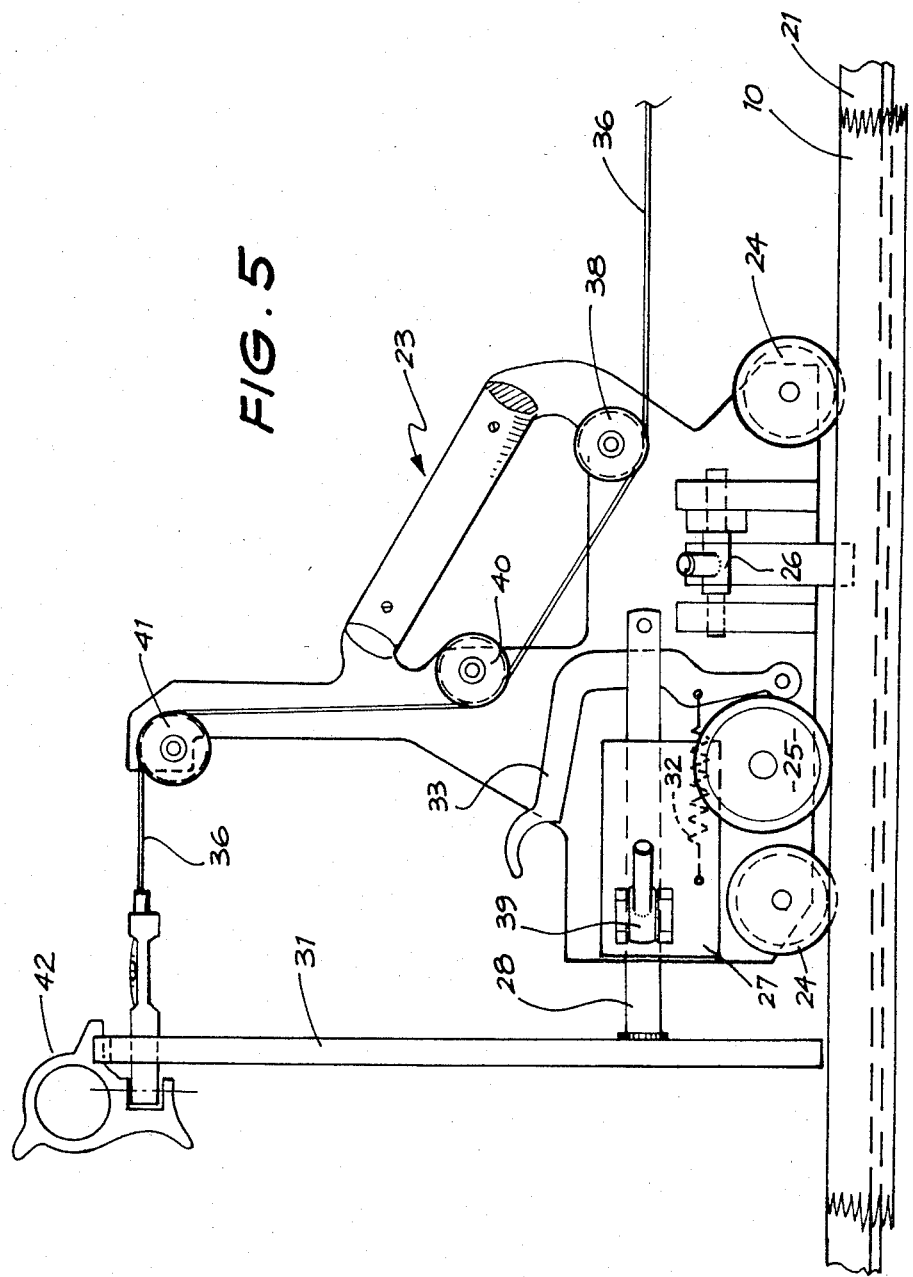
FIG. 5 is a side elevation of the movable carriage assembly.

A carriage 23 with two double-flanged wheels 24 runs along the top of the angle rail. It also has two plain outrigger wheels 25 which run on the timber table top to prevent it rocking sideways, see FIG. 3, and a floating-jaw clamp 26 (FIG. 5) which grips the sides of the rail 21 to enable the carriage 23 to be locked in any desired position along the table. The clamp 26 has rubber-covered fingers and is spring-actuated and cam-released to avoid over-tightening onto the aluminium rail 21. A bearing block 27 is mounted towards the front of the carriage 23. This contains a shaft 28 which is horizontal and can slide axially in the longitudinal direction of the table 10. Onto this shaft 28 is mounted a head contact plate 31. The rod has approximately 40 mm range of movement and is impelled forward by a spring 32. Its movement can be controlled by the operator via a control lever 33, and it can be clamped in any position within its range of movement by a cam-driven plunger 39.

Figure 2:
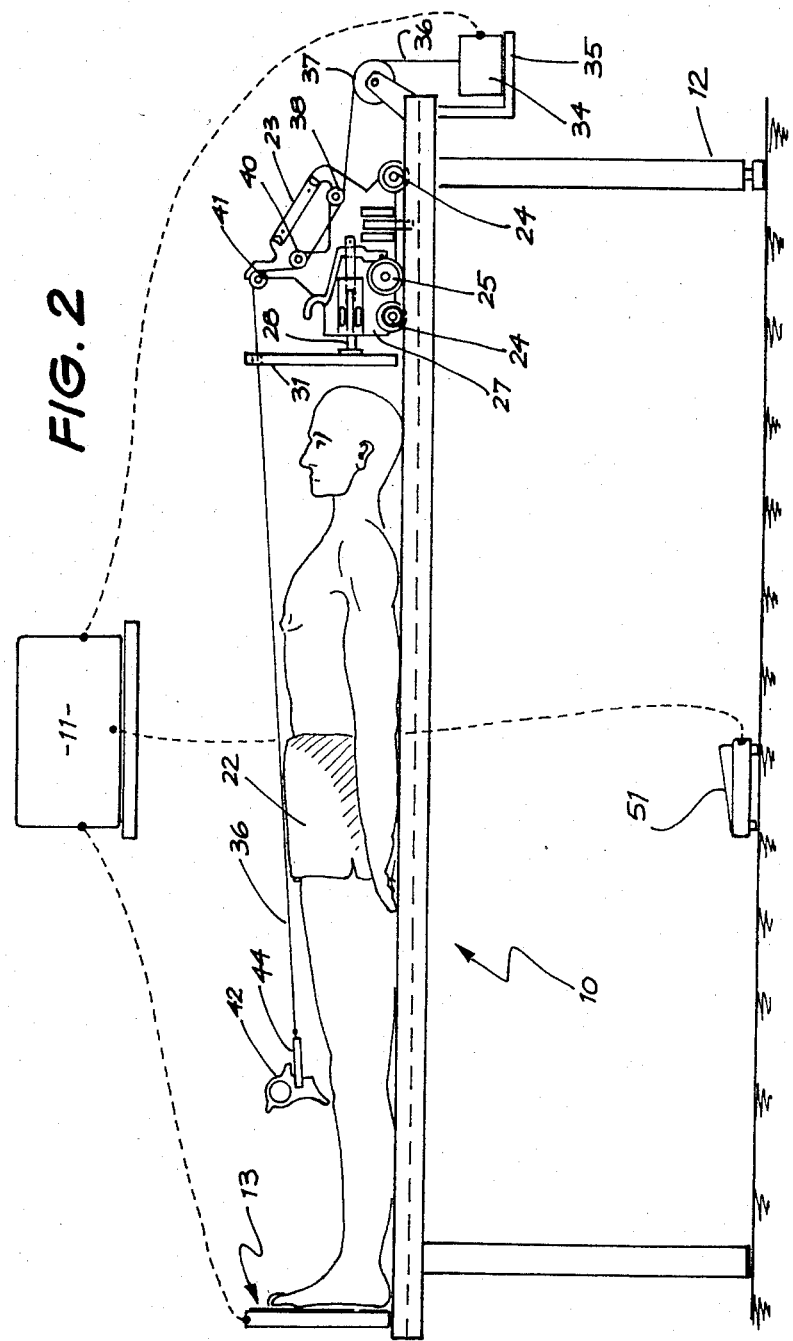
FIG. 2 is a view similar to FIG. 1 illustrating the use of the apparatus for the measurement of the position of a medial anatomic feature.
Figure 6:
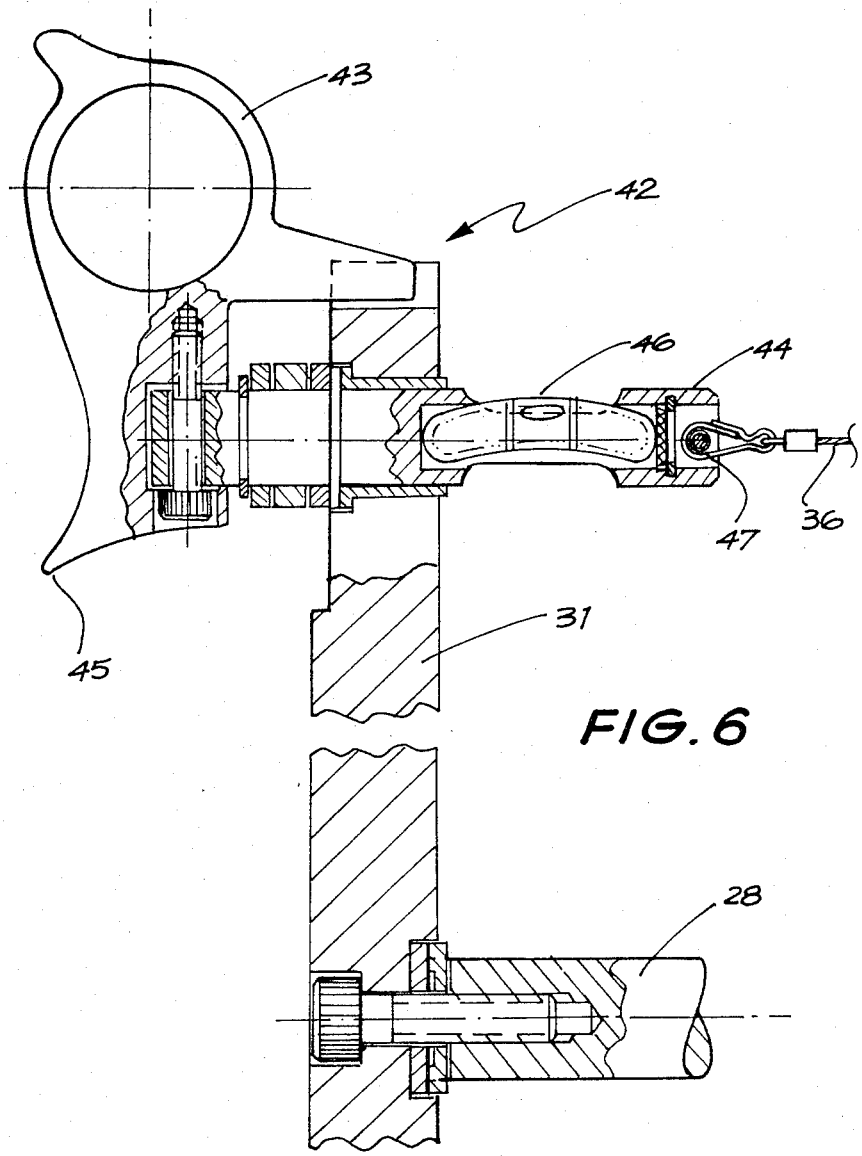
FIG. 6 is a part sectional view of the portions of the head contact plate assembly.

The transducer 34 which transforms the position along the table of the head contact plate 31 into an electrical signal is a proprietary type utilizing a multi-turn potentiometer. This has virtually infinite resolution and better than 0.5% linearity over the operating range. It is driven by a cable reel with spring retraction, and mounts on a bracket 35 at the head end of the table 10. The cable 36 passes vertically upwards from the transducer 34, which is mounted below the head end of the table, and makes a quarter-turn around a free-running and accurately mounted pulley 37, then passes horizontally along the table 10 above the rail 21 to the carriage 23. Here it passes over three pulleys 38, 40 and 31 and fixes to the rear of an assembly 42 (see FIG. 6) which locates in the head contact plate 31, above the position occupied by the subject's head, and which is drawn out over the subject (see FIG. 2) in order to measure the positions of other anatomical features. The system of spring-loaded transducer cable attaching effectively to the head contact assembly avoids all potential problems of magnified backlash, slippage, and pitching error due to uneven wear.

The nearly constant transducer reel-in force is lower than the spring force driving the head contact plate forward, and is low enough so that the carriage 23 can be moved forward without undue effort by the operator. The head contact force is low enough to be comfortable to the subject, and nearly constant over two ranges of movement of the carriage and the head contact plate spindle. A set of three calibration bars of lengths 800, 1400, and 2000 mm is provided to allow the calibration of the system to be checked periodically.

The assembly 42 located in the head contact plate 31 is manually drawn out over the subject to measure the position of medial anatomical features. It consists of a grasping ring 43 which is pivotally connected to a short stem 44, see FIG. 6, which terminate in a pointer 45 to align with the desired anatomical feature. Within the stem is a spirit level tube 46. The transducer cord 36 is connected to the rear end of this stem by a pivotal connection 47. The pivotal connection between the grasping ring 43 and the stem 44 prevents the stem 44 and the transducer cord being in other than straight line alignment in the horizontal plane, while allowing the pointer 45 to be held in a vertical plane, as indicated by the spirit level. This arrangement does not guarantee a completely straight-line alignment of transducer cord and stem in the withdrawn or usage state, or that the cord and stem are accurately normal to the foot contact plates 13. It does, however, serve to reduce the misalignment towards that of a small angle over the drawn-out length of the transducer cord, avoiding significant tilting of the pointer out of the transverse vertical plane. If a 3° misalignment existed over a drawn-out cord length of 75 cm, a position measurement error of 1 mm would result. While this feature of the system is recognised as having a somewhat higher possible error than that in the overall-length measurement mode, this was regarded as acceptable. Coherence between the readings obtained in the overall-length measurement mode and those taken with the draw-out pointer assembly is achieved by arranging the centre plane of the swing-down pointer to lie in the surface plane of the head contact plate when the draw-out assembly is stowed in position in the head contact plate, and it and the transducer cord all move as one.

Figure 3:
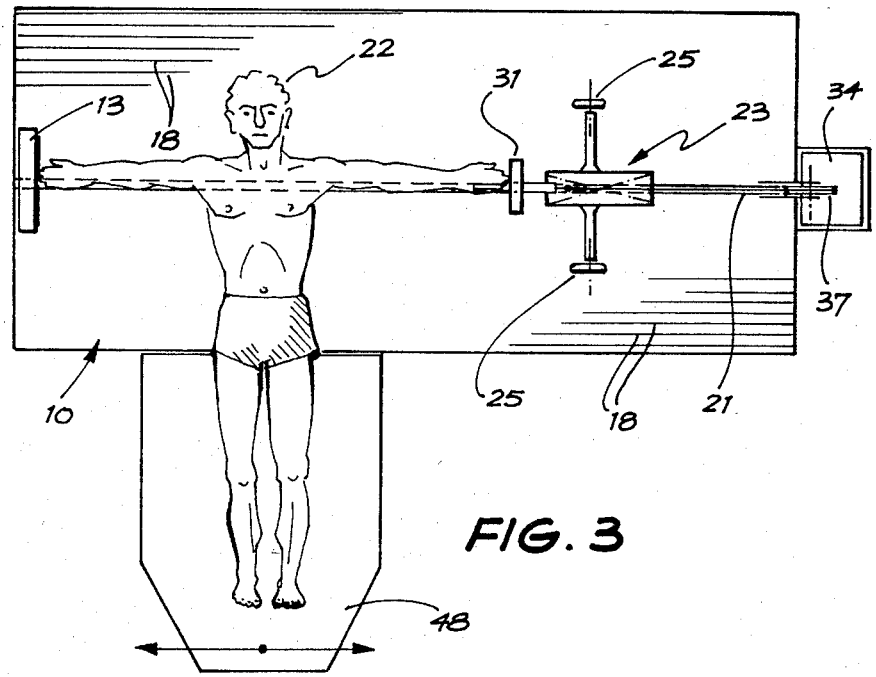
FIG. 3 illustrates the manner in which the apparatus can be adapted for use in making armspan measurements.

A side table 48 can be clipped into any convenient position along either side of the main table to allow a subject to be positioned transversely on the main table in order to measure the outstretched arm span, see FIG. 3.

The transducer 34 and a pedal switch 51 used to activate the measurement process connect to the foot contact box 13, and thence, together with the wiring to the switches in that box, to the console via a shielded cable. The console 11 contains the electric circuitry (see FIG. 7) including the main switch and fuse for the system, a regulated power supply for the transducer, the digital panel meter which provides the visual display, and the printer, as well as a low-voltage supply for the four foot position status lamps. These last are grouped on the console panel in a small square array which mimics the positions of the four plates on the foot contact box. The voltage signal from the transducer is passed via a buffer amplifier to the digital panel meter which provides a BCD output to the printer. A set of six digital switches on the console allows the date to be set so that the printer will print it together with the measured height in centimetres to one decimal place. Between the date and the height data a row of four asterisks will be printed if all four foot contact plates are properly depressed. If any asterisks are absent it is apparent which plate was not depressed, and the subject's position can be corrected before another reading is taken.

After attending to preliminaries such as switching on, setting the date and clamping the carriage in a position towards the head end of the table where it will not obstruct the subject, the satin sheet is placed on the portion of the table on which the subject will lie, so that it is well crumpled and has a large amount of gather. The subject mounts the table and lies on the back with the knees drawn up somewhat and the feet placed so that the MTP joints are touching the contact plates. A standard-thickenss pad can be placed under the head for comfort and to assist in the subsequent placement of the head into the Frankfurt plane. The knees are then steadily extended fully by the subject so that his or her trunk and head slide back along the table, with the relative movement being taken up by the gather in the satin sheet. It is this sliding backwards along the table which causes the residual frictional forces on the body to be compressive and thereby to generate a contact force at the feet.

In the final position the heels will be either resting on the table or close to it. The feet will be symmetrically placed on the foot contact box, as close together as any valgus tendency in the subject will comfortable allow. All four foot position status lamps on the console panel should now be illuminated, indicating proper foot contact with the plates at the heels and MTP joints. The position should now be with the subject centrally positioned on the table, which is checked in relation to the axial lines running along the table top. The operator guides the head into the Frankfurt plane and checks this using a square alongside the subject's head, against which the margins of the orbit and ear canal are viewed. If necessary the hair is combed away from the point which will be contacted by the head plate so that a significant thickness of hair is not included in the measurement.

The head contact plate and its spindle are locked in the retracted position in the carriage and the carriage is moved forward until the plate is within about 2 cms of the subject's head. The carriage is locked to the rail in this position, and the head contact plate is unclamped and allowed to move forward until it gently contacts the head. If the operator is satisfied that the subject's position is correct, the pedal switch is depressed to display and print the measurement. The spindle and head contact plate are then retracted and locked.

If measurements are required of other anatomical features, the draw-out assembly is drawn out of the head contact plate by the grasping ring, and the pointer is rotated into its downward pointing orientation. It is positioned over the relevant anatomical feature so that the spirit level tube shows correct alignment, and the pedal switch is again depressed to take the reading. The pointer is swung up again and the stem and grasping ring are returned to the head contact plate.

To measure arm span the subject is positioned on the side table (FIG. 3) so that the outstretched arms are along the centreline of the main table, with the fingertips of one hand just touching the foot contact plates. The carriage is advanced into proximity with the finger tips of the other hand and clamped. The head contact plate, which extends down close to the surface of the rail and the table, is advanced to touch the fingertips, and the foot pedal is pressed to take and record the measurement. The carriage is withdrawn to the head end of the table and clamped there. The subject dismounts.

The embodiment of the invention described above is given by way of example and as will be readily appreciated by those skilled in the art a variety of changes of design may be made within the general scope of the invention as defined above. For example the means of determining the position of the head plate may utilize an optical position sensing system rather than the mechanically operated transducer.

Whereas the invention has been described in connection with an embodiment in which the measurements are taken with the subject supine the essential features of the invention can be applied to a system in which the subject stands on a foot plate and a head plate is moved in a vertical direction to measure stature. In such an arrangement the apparatus can be adapted for use in arm length measurements by mounting the foot plate and the head plate on a support mounted on a wall by means of a pivotal mounting so that the support can be pivotted about a horizontal axis. It is considered, however, that the use of apparatus according to the invention in connection with subjects in a horizontal position presents many advantages over its use in a vertical position.

We claim:

1. An auxological measuring apparatus comprising a table having a flat, smooth horizontal surface, a foot contact means including a surface extending approximately normally to the surface of the table and against which the soles and heels of the feet of a human subject to be measured lying on the table are to be placed, means moveable linearly on the table surface selectively towards and away from the foot contact means and adapted to be brought into contact with the top of the subject's head, electronic transducer means associated with said moveable means constructed and arranged to produce an electric signal indicative of the distance between said moveable means and the surface of the foot contact means and thus of the height of the subject, electronic circuitry arranged to process said signal and provide a visible indication of said distance, said electronic transducer means being operable through a cable attached to the moveable means through graspable means removably attached to said moveable means and including a pointer, whereby the graspable means may be detached from the moveable means and utilized for measurement of the positions of medial anatomic features of the subject.

2. An auxological measuring apparatus as claimed in claim 1 wherein said foot contact means consists of four separate plates two being arranged for contact with the heels of the subject and two for contact with the MTP joints of the subject regardless of the size of the subject's feet, each plate being lightly spring loaded and hingedly mounted so that is deflects slightly under contact, an electric switch associated with each plate connected to said electronic circuitry and to visible indicator means, the arrangement being such that an indication is provided by said visible indicator means that a subject's feet are in proper contact with said foot contact means.

3. An auxological measuring apparatus as claimed in claim 1 or claim 2 wherein said moveable means consists of a carriage supported on wheels on the surface of the table and guided by guiding means thereon, means for fixing the carriage against movement, a head contact plate mounted on the carriage for movement towards or away from said foot contact means, releasable means for fixing said head contact plate against movement relative to said carriage and. spring means urging the head contact plate towards the foot contact means whereby, with the carriage fixed near the head of a subject, release of said releasable means allows the head contact plate to move into contact with the head of the subject under the influence of said spring means.

4. An auxological measuring apparatus as claimed in claim 3 wherein said grasping means includes a spirit level tube.

5. An auxological measuring apparatus as claimed in claim 1 wherein said table surface is overlaid by a well crumpled sheet of satin or like material to facilitate movement of the subject on the table surface.

6. An auxological measuring apparatus as claimed in claim 1 wherein a side table is removably and adjustably attached to said table to project at right angles thereto whereby an arm span measurement can be made of a subject lying on said table and side table with arms outstretched on the table between the foot contact means and said moveable means.

* * * * *